(12) United States Patent
Bischoff

(10) Patent No.: US 6,931,285 B2
(45) Date of Patent: Aug. 16, 2005

(54) DRIVE SHAFT SEAL FOR A MEDICAL ELECTRICAL LEAD

(75) Inventor: Thomas C. Bischoff, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 40 days.

(21) Appl. No.: 10/124,185

(22) Filed: Apr. 17, 2002

(65) Prior Publication Data

US 2002/0188338 A1 Dec. 12, 2002

Related U.S. Application Data

(60) Provisional application No. 60/284,430, filed on Apr. 17, 2001.

(51) Int. Cl.[7] ................................................. A61N 1/05
(52) U.S. Cl. ..................................................... 607/119
(58) Field of Search ................. 607/115–119, 122–128; 606/41

(56) References Cited

U.S. PATENT DOCUMENTS

| 4,106,512 A | 8/1978 | Bisping |
| 4,217,913 A | 8/1980 | Dutcher |
| 4,311,153 A | 1/1982 | Smits |
| 5,246,014 A | 9/1993 | Williams et al. |
| 5,259,394 A | 11/1993 | Bens |
| 5,456,708 A * | 10/1995 | Doan et al. .................. 607/127 |
| 5,531,780 A | 7/1996 | Vachon |
| 5,584,873 A | 12/1996 | Shoberg et al. |
| 5,948,015 A | 9/1999 | Hess et al. |
| 6,010,500 A * | 1/2000 | Sherman et al. ............... 606/41 |

* cited by examiner

*Primary Examiner*—George Manuel
(74) *Attorney, Agent, or Firm*—Girma Wolde-Michael; Michael C. Soldner

(57) ABSTRACT

A medical electrical lead that includes a lead body having a lead body lumen and an electrode head assembly having an inner wall and an electrode head assembly lumen adjacent to the lead body lumen. The lead further includes a drive shaft that extends through the lead body lumen and the electrode head assembly lumen, and a sealing member, having an outer diameter corresponding to the inner wall of the electrode head assembly lumen. The sealing member includes an inner lumen that receives the drive shaft, an outer sealing member that is fixedly engaged with the inner wall of the electrode head assembly, and an inner sealing member engaged with the drive shaft to provide a low friction seal.

2 Claims, 4 Drawing Sheets

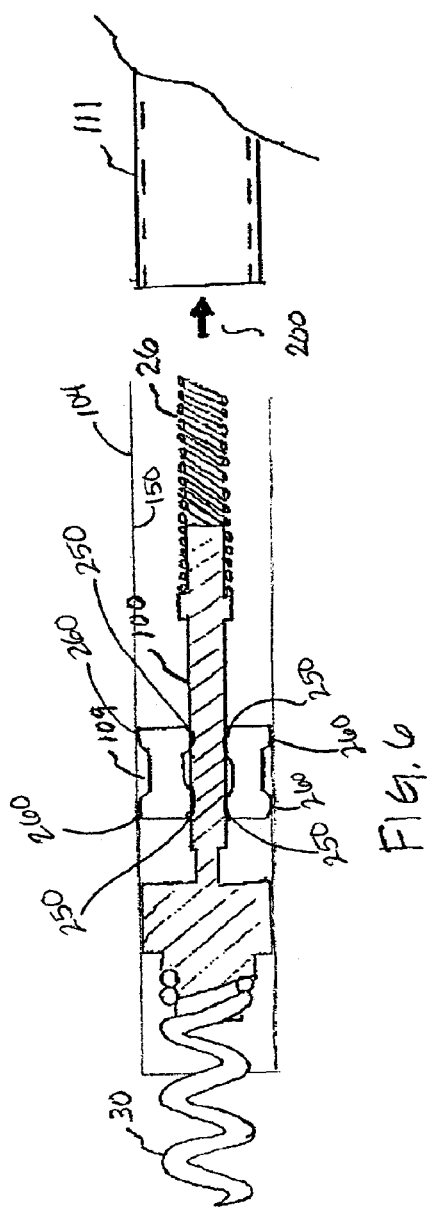

DRIVE SHAFT SEAL FOR A MEDICAL ELECTRICAL LEAD

REFERENCE TO PRIORITY APPLICATION

This application claims the benefit of U.S. Provisional Application No. 60/284,430 filed on Apr. 17, 2001, entitled "MEDICAL ELECTRICAL LEAD", incorporated herein by reference in its entirety.

CROSS-REFERENCE TO RELATED APPLICATIONS

Cross-reference is hereby made to commonly assigned related U.S. Applications, filed concurrently herewith, entitled "INSULATING MEMBER FOR A MEDICAL ELECTRICAL LEAD AND METHOD FOR ASSEMBLY"; P-10012, entitled "IMPLANTABLE MEDICAL LEAD HAVING A RETRACTION STOP MECHANISM"; P-10013, entitled "APPARATUS FOR TRANSFERRING TRACTION FORCES EXERTED ON AN IMPLANTABLE MEDICAL LEAD"; and P-10051, entitled "MEDICAL ELECTRICAL LEAD".

FIELD OF THE INVENTION

The present invention relates generally to a medical electrical lead, and, more particularly, the present invention relates to an implantable lead having a seal for preventing the ingress of body fluids into the lumen of a lead body.

BACKGROUND OF THE INVENTION

A wide assortment of implantable medical devices (IMDs) are presently known and in commercial use. Such devices include cardiac pacemakers, cardiac defibrillators, cardioverters, neurostimulators, and other devices for delivering electrical signals to a portion of the body and/or receiving signals from the body. Pacemakers, for example, are designed to operate so as to deliver appropriately timed electrical stimulation signals when needed, in order to cause the myocardium to contract or beat, and to sense naturally occurring conduction signals in the patient's heart.

Devices such as pacemakers, whether implantable or temporary external type devices, are part of a system for interacting with the patient. In addition to the pacemaker device, which typically has some form of pulse generator, a pacing system includes one or more leads for delivering generated signals to the heart and for sensing cardiac signals and delivering those sensed signals from the heart back to the pacemaker. As is known, pacemakers can operate in either a unipolar or bipolar mode, and can pace the atria or the ventricles. Unipolar pacing requires a lead having only one distal electrode for positioning in the heart, and utilizes the case, or housing of the implanted device as the other electrode for the pacing and sensing operations. For bipolar pacing and sensing, the lead typically has two electrodes, one disposed substantially at the distal tip end of the lead, and the other spaced somewhat back from the distal end. Each electrode is electrically coupled to a conductive cable or coil, which carries the stimulating current or sensed cardiac signals between the electrodes and the implanted device via a connector.

Combination devices are available for treating cardiac arrhythmias that are capable of delivering electrical shock therapy for cardioverting or defibrillating the heart in addition to cardiac pacing. Such a device, commonly known as an implantable cardioverter defibrillator or "ICD", uses coil electrodes for delivering high-voltage shock therapies. An implantable cardiac lead used in combination with an ICD may be a quadrapolar lead equipped with a tip electrode, a ring electrode, and two coil electrodes. A quadrapolar lead requires four conductors extending the length of the lead body in order to provide electrical connection to each electrode.

In order to perform reliably, cardiac pacing leads need to be positioned and secured at a targeted cardiac tissue site in a stable manner. One common mechanism for securing an electrode position is the use of a rotatable fixation helix. The helix exits the distal end of the lead and can be screwed into the body tissue. The helix itself may serve as an electrode or it may serve exclusively as an anchoring mechanism to locate an electrode mounted on the lead adjacent to a targeted tissue site. The fixation helix may be coupled to a drive shaft that is further connected to a coiled conductor that extends through the lead body as generally described in U.S. Pat. No. 4,106,512 to Bisping et al. A physician rotates the coiled conductor at a proximal end to cause rotation of the fixation helix via the drive shaft. As the helix is rotated in one direction, the helix is secured in the cardiac tissue. Rotation in the opposite direction removes the helix from the tissue to allow for repositioning of the lead at another location.

When using such a lead, it is desirable to prevent the ingress of body fluids into the lead body. Blood or other body fluids entering the lead body can create a pathway for infection, a serious complication for implantable devices. Furthermore, the entrance of blood into the lumen of a lead body can interfere with the insertion of a stylet used for lead positioning during implantation and with the final connection of the lead to an implantable medical device.

Methods for sealing the distal end of the lead body while still allowing a coiled conductor and drive shaft to rotate for advancing or retracting a fixation helix are known. One method is to provide a sealing membrane within the lumen of the distal lead tip. Reference is made to U.S. Pat. No. 4,311,153 issued to Smits. When the helix is advanced, the pointed tip of the fixation helix punctures the sealing membrane, which provides a seal around the fixation helix. When used during implantation, multiple turns of the coil may be required in order to build up torque to overcome the friction encountered when rotating the helix through the membrane. The helix may not advance by the same amount with each turn applied to the coil. Therefore, the extension or retraction of the helix may be somewhat unpredictable. The punctured membrane may not always form a fluid-tight seal around the fixation helix.

Another method for sealing the lumen of a medical lead involves positioning a sealing ring to encircle the drive shaft connected to the fixation helix. This type of seal may be maintained in a desired location by retainers mounted proximal and distal to the seal. Reference is made to U.S. Pat. No. 5,948,015 issued to Hess et al.

Pacemaker systems, as well as other medical devices such as those mentioned above, can utilize a wide variety of lead designs. Many considerations are taken into account when optimizing the design of a lead. For example, minimizing lead size is important since a smaller device is more readily implanted within the cardiac structures or coronary vessels of a patient. Moreover, providing features that make a lead easier to implant and extract allows the clinician to complete the associated surgical procedure more safely and in less time. Finally, an optimized lead design requires a minimum number of parts that may be assembled using techniques that are relatively simple and low cost.

A medical lead having an improved seal against body fluids and which allows precise control over the rate of advancement of a fixation helix is therefore needed. Furthermore, such a seal should not require difficult or costly lead manufacturing techniques. The improved seal preferably is capable of withstanding the high pressures encountered within the heart so that, when the lead is used in conjunction with implantable pacemakers or ICDs, blood does not enter the lead lumen and interfere with the implant procedure or cause infection.

SUMMARY OF THE INVENTION

The present invention is directed to a medical electrical lead that includes a lead body having a lead body lumen and an electrode head assembly having an inner wall and an electrode head assembly lumen adjacent to the lead body lumen. The lead further includes a drive shaft that extends through the lead body lumen and the electrode head assembly lumen, and a sealing member, having an outer diameter corresponding to the inner wall of the electrode head assembly lumen. The sealing member includes an inner lumen that receives the drive shaft, an outer sealing member that is fixedly engaged with the inner wall of the electrode head assembly, and an inner sealing member engaged with the drive shaft to provide a low friction seal.

BRIEF DESCRIPTION OF THE DRAWINGS

FIG. 4 is a perspective view of a drive shaft seal according to the present invention;

FIG. 5 is a sectional view of a drive shaft seal according to the present invention;

FIG. 6 is a plan view of a drive shaft and drive shaft seal used in assembling the distal end of the lead shown in FIG. 3.

FIG. 7 is a side, cut-away view of the drive shaft seal shown in FIG. 4.

DETAILED DESCRIPTION OF THE INVENTION

Figure 1:
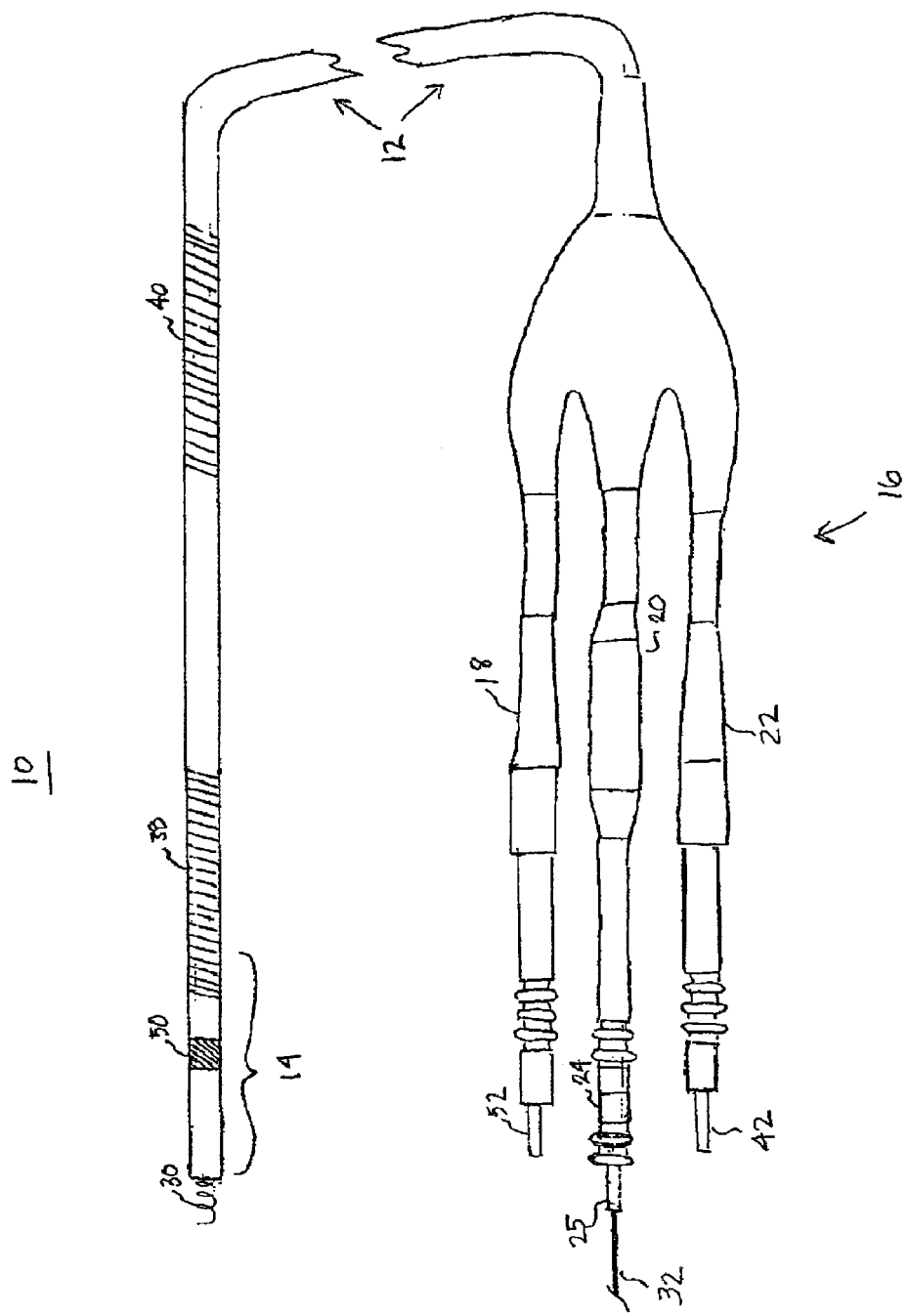
FIG. 1 is a plan view of an implantable cardiac lead utilized in accordance with the present invention.

FIG. 1 is a plan view of an implantable cardiac lead utilized in accordance with the present invention, embodied as a transvenous cardiac defibrillation lead. As illustrated in FIG. 1, a lead 10 according to the present invention includes an elongated lead body 12 having a connector assembly 16 at a proximal end of lead 10 for connecting to an implantable device and an electrode head assembly 14 at a distal end of lead 10 for carrying one or more electrodes. Lead 10 is shown as a quadrapolar lead including a helical tip electrode 30, a ring electrode 50, a right ventricular (RV) defibrillation coil 38 and a superior vena cava (SVC) defibrillation coil 40. The helical tip electrode 30 and ring electrode 50 may be utilized to sense cardiac signals and/or deliver pacing pulses to a patient. One of the defibrillation coils 38 and 40 serves as the cathode while the other serves as the anode during delivery of a defibrillation shock to a patient as a result of a detected tachycardia or fibrillation condition.

The lead body 12 takes the form of an extruded tube of biocompatible plastic such as silicone rubber. Multiple lumens located within the lead body 12 carry four insulated conductors from the connector assembly 16 to the corresponding electrodes 30, 50, 38 and 40 located at or near the distal end of the lead 10. The multi-lumen lead body 12 may correspond generally to that disclosed in U.S. Pat. No. 5,584,873 issued to Shoberg et al. Three of the insulated conductors carried by lead body 12 are stranded or cabled conductors, each electrically coupled to one of the ring electrode 50, the RV coil 38 and the SVC coil 40. The cabled conductors may correspond generally to the conductors disclosed in U.S. Pat. No. 5,246,014, issued to Williams et al., incorporated herein by reference in its entirety. A fourth, coiled conductor extends the length of the lead body 12 and is coupled to the helical tip electrode 30.

In this embodiment, the helical tip electrode 30 functions as an electrode for cardiac pacing and/or sensing and as an active fixation device for anchoring the lead 10 in a desired position. In other embodiments that may employ the present invention, a helical tip may function only as an active fixation device. Reference is made to U.S. Pat. No. 4,217,913 to Dutcher, incorporated herein by reference in its entirety. Therefore, the helical tip electrode 30 may also be referred to herein as a "fixation helix."

The connector assembly 16 has multiple connector extensions 18, 20, and 22 arising from a trifurcated connector sleeve, typically formed of silicone rubber. The connector extensions 18, 20, and 22 couple the lead 10 to an implantable medical device such as an implantable cardioverter defibrillator (ICD).

Connector extension 20 is shown as a bi-polar connector including a connector ring 24 and a connector pin 25. Connector extension 20 houses the cabled conductor that is electrically coupled to the connector ring 24 at its proximal end and to the ring electrode 50 at its distal end. The connector extension 20 also houses the coiled conductor that is electrically coupled to the connector pin 25 and extends to the tip electrode 30. During a lead implant or explant procedure, rotation of the connector pin 25 relative to the connector assembly 16 causes corresponding rotation of the coiled conductor and advancement or retraction of the helical tip electrode 30 in the fashion generally described in U.S. Pat. No. 4,106,512 to Bisping et al., incorporated herein by reference in its entirety. By advancing the helical tip electrode 30, the electrode 30 can be actively fixed in cardiac tissue. A stylet 32 may be advanced within an inner lumen of the coiled conductor to the distal end of the lead 10 to aid in lead placement during an implant procedure.

The connector extension 18 carries a single connector pin 52 that is electrically coupled to an insulated cable extending the length of the lead body 12 and electrically coupled to the RV coil 38. The connector extension 22 carries a connector pin 42 that is electrically coupled to a respective insulated cable that is further coupled to the SVC coil 40.

Figure 2:
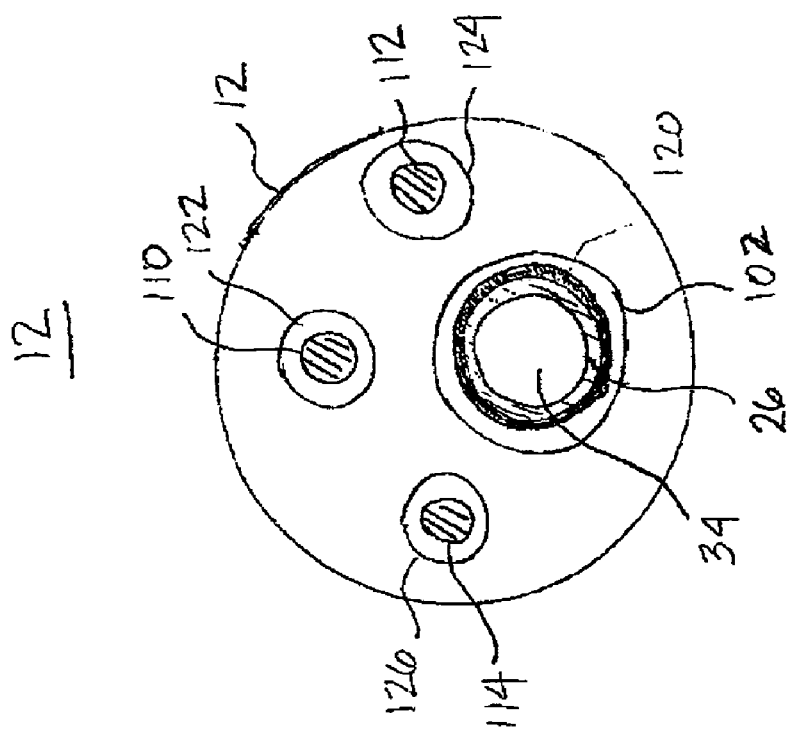
FIG. 2 is a sectional view of a multi-lumen lead body of the lead shown in FIG. 1.

FIG. 2 is a cross-sectional view of a multi-lumen lead body of the lead shown in FIG. 1. As illustrated in FIG. 2, lead body 12 includes four lumens 102, 122, 124, and 126. Lumen 102 carries the coiled conductor 26. The conductor 26 is shown surrounded by an insulation tubing 120. A stylet 32 may be advanced within the lumen 34 of the coiled conductor 26. Lumen 122 carries an insulated cable 110 that is electrically coupled at a proximal end to the connector ring 24 and at a distal end to the ring electrode 50. Lumen 124 carries an insulated cable 112 that is electrically coupled at a proximal end to the connector pin 52 and at a distal end to the RV coil 38. Lumen 126 carries an insulated cable 114 that is electrically coupled at a proximal end to the connector pin 42 and at a distal end to the SVC coil 40.

Figure 3:
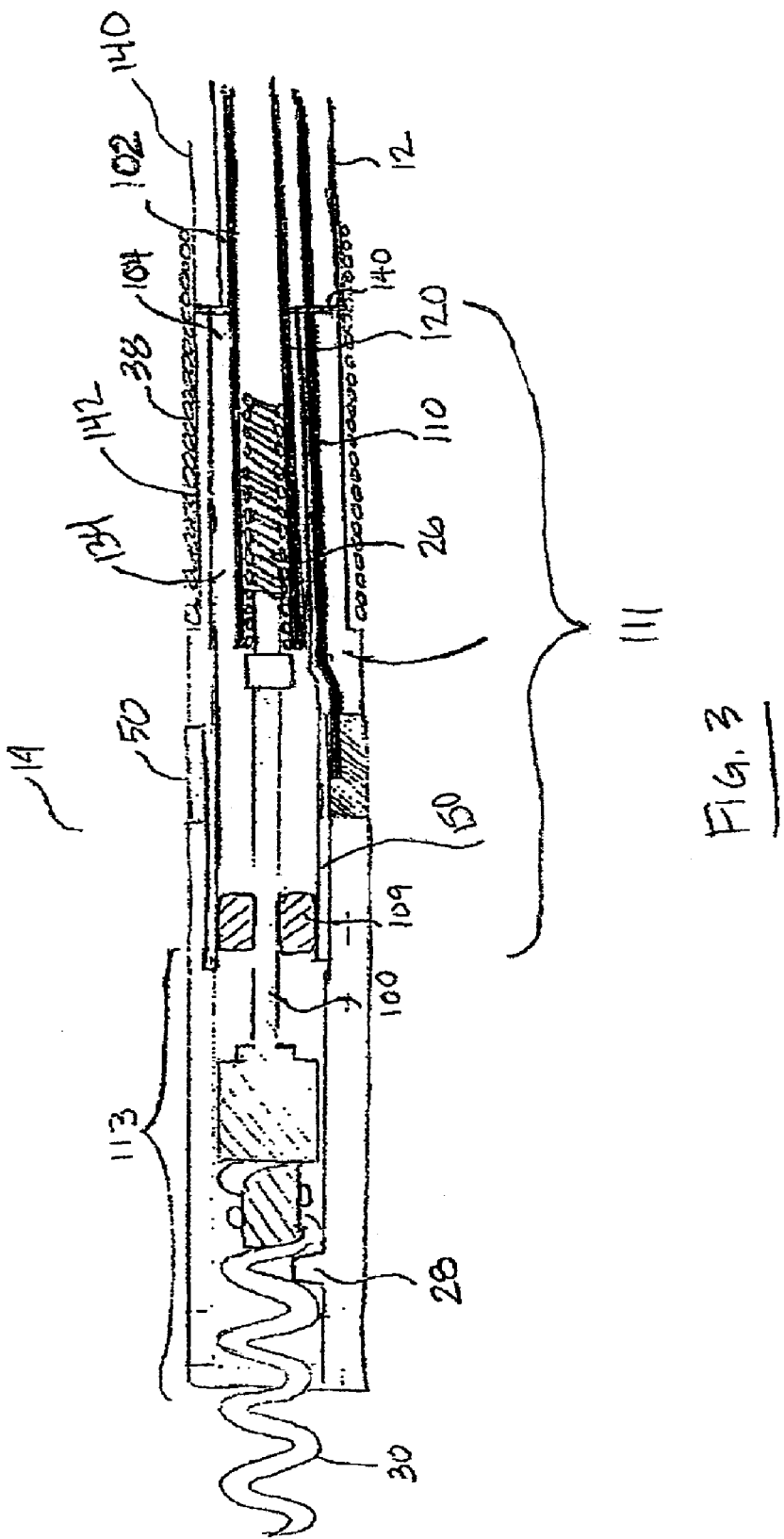
FIG. 3 is a side cut away view of a distal end of the lead shown in FIG. 1.

FIG. 3 is a side cutaway view of the distal end of the lead 10 showing a detailed view of the electrode head assembly 14 and the electrodes 30, 50 and 38. The molded, tubular electrode head assembly 14 includes two members, a distal electrode head assembly 113 and a proximal electrode head assembly 111. The distal and proximal electrode head assemblies 113 and 111 are preferably formed from a relatively rigid biocompatible plastic. For example, assemblies 113 and 111 may be fabricated from molded polyurethane. The proximal electrode head assembly 111 is coupled to the multi-lumen lead body 12, typically formed from a relatively more compliant plastic such as silicone rubber, at a joint 140. The lumen 104 within the proximal electrode head assembly 111 communicates with the lumen 102 within the lead body 12 for carrying the coiled conductor 26 extending between the tip electrode 30 and the connector ring 26. In FIG. 3, the ring electrode 50 is shown coupled to the cable 110, and the RV coil 38 is shown positioned on the outer diameter of the proximal electrode head assembly 111 and the lead body 12.

FIG. 3 further shows the helical tip electrode 30 electrically coupled to the coiled conductor 26 via a drive shaft 100. The electrode 30 and drive shaft 100 are preferably fabricated of a biocompatible metal such as platinum iridium alloy. The coiled conductor 26 extends to the proximal connector assembly 16. Rotation of the connector pin 25 at the proximal end of coiled conductor 26 causes corresponding rotation of the distal end of the coiled conductor 26 to, in turn, cause rotation of the drive shaft 100. This rotation results in extension or retraction of helical tip electrode 30. A guide 28 actuates the helical tip 30 as it is advanced or retracted. In accordance with the present invention, the lead 10 includes a drive shaft seal 109 encircling the drive shaft 100. The drive shaft seal 109, which may be formed of silicone or any other elastomer, is housed within the electrode head assembly 14.

FIG. 4 is a perspective view of a drive shaft seal according to the present invention. As illustrated in FIG. 4, the drive shaft seal 109 includes two outer sealing rings 260 located substantially at each end of the seal 109. It is recognized that any number of outer sealing rings may be provided any where along the length of seal 109. These outer sealing rings 260 form a high-friction seal with the inner diameter of the electrode head assembly 14.

In particular, as illustrated in FIG. 4, an outer diameter 258 of the seal 109 has a "D" shape. This "D" shape, which is also shown by the sectional view of FIG. 5, matches a "D" shaped inner diameter of the electrode head assembly 14. The seal 109 has a circular inner lumen 252, through which the drive shaft 100 passes. According to the present invention, the particular shape of the outer diameter 258 may be of any shape that corresponds to the inner diameter of the electrode head assembly 14. Interference between the outer diameter 258 and the inner diameter of electrode head assembly 14 prevents shifting or rotation of the seal 109 relative to the electrode head assembly 14 when the drive shaft 100 is rotated within circular lumen 252. The outer sealing rings 260 are sized to provide a press fit so that the outer sealing rings 260 are fixedly engaged against an inner wall 150 of the lumen 104 of electrode head assembly 14, creating a seal along inner wall capable of withstanding pressures that may be typically encountered within the cardiovascular system.

FIG. 6 is a plan view of a drive shaft and a drive shaft seal used in assembling a distal end of the lead, according to the present invention. As illustrated in FIG. 6, the drive shaft seal 109 is positioned over the drive shaft 100 prior to welding the coiled conductor 26 to the proximal portion of the shaft 100. Then the proximal, non-welded end of the coiled conductor 26 is inserted in the tubular electrode head assembly 14 as indicated by the arrow 200. The coiled conductor 26 and the drive shaft 100 are advanced within the electrode head assembly 14 until the seal 109 is fit within the electrode head assembly 14, in a position as shown in FIG. 3. Because the drive shaft seal 109 is retained within the electrode head assembly 14 via a friction fit, assembling the lead 10 with the seal 109 does not require additional parts or bonding methods. As a result, fewer manufacturing faults occur during lead production, manufacturing cost is decreased, and the assembly process is made simpler.

FIG. 7 is a side, cut-away view of a drive shaft seal according to the present invention. As illustrated in FIG. 7, the shaft seal 109 according to the present invention includes two inner sealing rings 250 that flexibly conform to the drive shaft 100. The inner sealing rings 250 are shown located substantially at each end of the seal 109, but it is recognized that any number of sealing rings may positioned any where along the length of the seal 109 within the inner lumen 252. The inner sealing rings 250 are shown to be semi-circular in cross-section in FIG. 7, however the inner sealing rings 250 may be of any geometrical shape in cross-section, such as square, rectangular or otherwise, that still provides an acceptable sealing interface with the drive shaft 100. Likewise, the two outer sealing rings 260 are not limited to having the cross-sectional geometry illustrated in FIG. 7 but could have any geometrical shape that provides an acceptable sealing interface with the head electrode head assembly 14.

Because the inner sealing rings 250 provide a low friction seal when engaged against the drive shaft 100, the drive shaft 100 is allowed to rotate without encountering an undue amount of friction. As a result, the coiled conductor 26 used to rotate the drive shaft 100 may be constructed with smaller, more responsive coils. Smaller coil diameter results in an overall reduced lead body size. The low friction seal provided by the inner sealing rings 250 allows for the linear or near-linear transfer of torque from the proximal end of coiled conductor 26 to the helical tip 30, making helix extension easy to control, while stopping ingress of fluid within the lumen 104 electrode head assembly 14, while allowing rotation of the drive shaft 100 within the inner lumen 252.

As illustrated in FIGS. 4 and 7, drive shaft seal 109 includes a distal portion 264 and a proximal portion 266. According to the present invention, the drive shaft seal 109 is molded so that the outer sealing rings 260 are form with an outer edge 268 that is square, so that parting lines 270 corresponding to the distal portion 264 and the proximal portion 266 are perpendicular to an axis 272 extending through the inner lumen 252 of the drive shaft seal 109, and the mold used during the molding process is parted along the squared outer edge 268. As a result, the drive shaft seal 109 of the present invention provides a robust seal by avoiding potential breaks in the seal at the outer sealing rings 260.

In addition, inner sealing rings 250 of the drive shaft seal 109 of the present invention are positioned to be aligned with opposite positioned outer sealing rings 260. As a result, the drive shaft 100 exerts a force on the inner sealing rings 250 which is translated directly to the corresponding oppositely positioned outer sealing rings 260, while at the same time inner wall 150 of lumen 104 exerts a force on the outer sealing rings 260 which is translated directly to corresponding oppositely positioned inner sealing rings 250. As a result, localized pressure at the seal formed between the outer sealing rings 260 and the inner wall 150, and between the drive shaft 100 and the inner sealing rings 250 is stabilized, improving the seal formed by the inner sealing rings 250 and the outer sealing rings 260.

The drive shaft seal is formed from a resilient, supple material, preferably silicone rubber. The volume of the seal is made as large as possible within the available space of the electrode head assembly in order to increase the compliance of the seal and provide a tightly pressed fit within the electrode head assembly, thereby improving the effectiveness of the seal. A large surface area on the outer diameter of the seal provides interference with the adjacent electrode head assembly creating a high-friction fit that prevents shifting of the seal. A lower surface area on the inner diameter of the seal provides a low-friction interface with the drive shaft, allowing the shaft to easily rotate within the seal.

The present invention thus provides a reliable seal against body fluids in an implantable medical lead. The seal further provides a low-friction interface with a rotatable drive shaft such that less torque is needed to advance the helix than with prior known sealing methods. This low-friction interface allows predictable linear advancement of the fixation helix with each turn applied to a coiled conductor. The low-friction seal further allows the coiled conductor to be made from smaller coils, reducing overall lead size. The seal provided by the present invention is easy to assemble since no additional parts or bonding methods are required.

The lead described above employing a drive shaft seal in accordance with the present invention is a quadrapolar high-voltage lead of the type that may be used for pacing, cardioversion and defibrillation. However, it will be understood by one skilled in the art that any or all of the inventive aspects described herein may be incorporated into other types of lead systems. For example, one or more of the aspects of the drive shaft seal described herein may be included in any unipolar or multipolar pacing lead having a rotatable drive shaft and any combination of one or more tip, ring or coil electrodes for use in pacing, sensing, and/or shock delivery. Alternatively, any drug-delivery or other electrical stimulation lead that benefits from having a sealed lumen may employ aspects of the current inventive lead system. As such, the above disclosure should be considered exemplary, rather than limiting, with regard to the following claims.

What is claimed is:

1. A medical electrical lead, comprising:
   a lead body having a lead body lumen;
   an electrode head assembly having an inner wall forming an electrode head assembly lumen adjacent to the lead body lumen;
   a drive shaft extending through the lead body lumen and the electrode head assembly lumen; and
   a sealing member including an outer diameter corresponding to the inner wall of the electrode head assembly, a first end, a second end, an inner lumen extending from the first end to the second end and receiving the drive shaft, a first inner sealing ring positioned in proximity to the first end and a second inner sealing ring positioned in proximity to the second end; wherein the first sealing ring and the second sealing ring engage the drive shaft in a low friction seal, and wherein the sealing member further includes a first outer sealing ring and a second outer sealing ring, the first sealing ring and the second sealing ring forming a high friction seal with the inner wall of the electrode head assembly.

2. The lead of claim 1, wherein the first outer sealing ring is positioned in proximity to the first end of the sealing member, approximately aligned with the first inner sealing ring, and the second outer sealing ring is positioned in proximity to the second end, approximately aligned with the second inner sealing ring.

* * * * *